US006372248B1

(12) United States Patent
Qin et al.

(10) Patent No.: US 6,372,248 B1
(45) Date of Patent: *Apr. 16, 2002

(54) DEHYDRATED HYDROGELS

(75) Inventors: Yimin Qin, Northwich; Denis Keith Gilding, Winsford, both of (GB)

(73) Assignee: Innovative Technologies Limited, Cheshire (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/809,685

(22) PCT Filed: Oct. 30, 1995

(86) PCT No.: PCT/GB95/02543

§ 371 Date: May 30, 1997

§ 102(e) Date: May 30, 1997

(87) PCT Pub. No.: WO96/13285

PCT Pub. Date: May 9, 1996

(30) Foreign Application Priority Data

Oct. 28, 1994 (GB) ............................................. 9421967
Aug. 18, 1995 (GB) ............................................. 9516933

(51) Int. Cl.⁷ .......................... A61F 13/00; A61F 15/00
(52) U.S. Cl. ...................... 424/443; 424/449; 424/486; 424/487; 424/485; 424/488
(58) Field of Search .............................. 252/194, 315.1, 252/315.3, 315.4; 602/45, 49, 56, 900; 428/403, 407; 424/445, 485, 488, 493, 494, 496, 443, 78.06, 449, 486, 487; 524/916; 260/DIG. 31

(56) References Cited

U.S. PATENT DOCUMENTS

| 4,393,048 A | * | 7/1983 | Mason, Jr. et al. | 424/445 |
| 5,197,945 A | * | 3/1993 | Cole et al. | 602/49 |
| 5,238,685 A | * | 8/1993 | Wren | 424/445 |
| 5,246,708 A | * | 9/1993 | VonBorstel et al. | 424/450 |
| 5,409,703 A | * | 4/1995 | McAnalley et al. | 424/435 |
| 5,482,932 A | * | 1/1996 | Thompson | 424/445 |
| 5,607,760 A | * | 3/1997 | Roe | 442/375 |
| 5,670,169 A | * | 9/1997 | Cornell et al. | 424/488 |
| 5,836,970 A | * | 11/1998 | Panndit | 606/213 |
| 5,914,124 A | * | 6/1999 | Mahoney et al. | 424/445 |
| 5,980,930 A | * | 11/1999 | Fenton et al. | 424/445 |
| 5,981,821 A | * | 11/1999 | Barikosky | 424/445 |
| 5,986,164 A | * | 11/1999 | Kershaw et al. | 602/49 |
| 6,080,420 A | * | 6/2000 | Qin et al. | 424/443 |
| 6,203,845 B1 | * | 3/2001 | Qin et al. | 427/2.31 |

FOREIGN PATENT DOCUMENTS

| EP | 0216378 | * | 4/1987 |
| EP | 0243069 | * | 10/1987 |
| GB | 1329693 | * | 9/1973 |
| GB | 1394741 | * | 5/1975 |
| WO | WO90/11820 | * | 10/1990 |
| WO | WO91/11206 | * | 8/1991 |

OTHER PUBLICATIONS

PTO–01–116, Translation of EP 0 216 378, Hemostatic Material and Its Manufacture (USPTO, Wash, DC, Oct. 2000).*

Database WPIDS on STN, week 8313, London:Derwent Publications Ltd., AN –87–088078, Class A11, EP 0 216 378 A (Mozisek) abstract, 1987.*

* cited by examiner

Primary Examiner—Daniel S. Metzmaier
(74) Attorney, Agent, or Firm—Clifford W. Browning; Woodard, Emhardt, Naughton, Moriarty & McNett

(57) ABSTRACT

A dehydrated hydrogel incorporating a plasticiser and fibers which have provided cations for cross-linking the dehydrated hydrogel.

23 Claims, No Drawings

DEHYDRATED HYDROGELS

This application is filed under 35 USC §371 and is based on PCT/GB95/02543, filed Oct. 30, 1995.

The present invention relates to dehydrated hydrogels which are useful in the treatment of wounds.

BACKGROUND OF THE INVENTION

A hydrogel is a cross-linked macromelecular network swollen with water or biological fluids. A dehydrated hydrogel is a cross-linked macro-molecular network that will swell to form a hydrogel upon contact with water or biological fluids. Due to their 'dehydrated' condition, dehydrated hydrogels are easy to store and transport. In addition, when applied in the dry state to a wound they behave as superabsorbent materials.

SUMMARY OF THE INVENTION

According to a first aspect of the present invention there is provided a dehydrated hydrogel incorporating a plasticiser and fibres which have provided cations for cross-linking the dehydrated hydrogel.

According to a second aspect of the present invention there is provided a method of producing a dehydrated hydrogel comprising dispersing fibres into an aqueous solution of a hydrogel precursor material incorporating a plasticiser, the fibres incorporating cations which are capable of cross-linking said precursor material to form a hydrogel, and evaporating water to produce a dehydrated hydrogel which incorporates said fibres, the dehydrated hydrogel being cross-linked by said cations.

The dehydrated hydrogel may be in the form of a film having a thickness of, for example, 20 microns to 1 mm.

The dehydrated hydrogels of the invention have a number of advantages. In particular, the presence of the fibres imparts strength and dimensional stability to the dehydrated hydrogel. Furthermore films of the dehydrated hydrogels have the property of swelling in only the thickness dimensions and not in the other two dimensions (as compared to films of conventional dehydrated hydrogels which swell in all three dimensions).

Typically, dehydrated hydrogels in accordance with the invention will comprise (based on the total weight of the fibres, polymer forming the hydrogel, and plasticiser, i.e. excluding water and other components) 15 to 40% by weight of fibres, 10 to 35% by weight of polymer, and 5 to 75% plasticiser. More preferably the fibres and polymer together provide about 40–60% ideally about 50% by weight on the same weight basis so that correspondingly the plasticiser provides 60–40%, ideally about 50%. Generally the amount of fibres will exceed the amount of polymer. For example the weight ratio may be 1.5–3:1. Typically the dehydrated hydrogel will contain less than 50% by weight of water, ideally less than 20%, based on the total weight of the dehydrated hydrogel.

Examples of hydrogel precursor material which may be used include sodium alginate, sodium carboxymethyl cellulose, sodium pectinate, sodium O-carboxymethyl chitosan (OCC), sodium N,O-carboxymethyl chitosan (NOCC), sodium polyacrylate, and naturally occurring gums and synthetic polymers containing pendant carboxylic acid groups.

The hydrogel precursor may consist wholly or partially of acemannan (or other component of Alloe Vera) which is a natural polymer known to accelerate healing of wounds. The acemannan may, for example, provide up to 80% of the matrix. The acemannan may be clinical grade material obtainable from Carrington Laboratories, Dallas, Tex., U.S.A.

The fibres which are used contain a di- or higher valent cation which is effective for cross-linking the hydrogel. Examples of suitable cations include $Ca^{2+}$, $Zn^{2+}$, and cations which also act as enzyme cofactors. Particular preferred examples of fibres which may be used are calcium alginate fibres. The fibres will generally have a length of 1 to 80 mm and a thickness of 10 to 50 microns.

The fibres may be such that they absorb water from the aqueous solution of the hydrogel precursor material during manufacture of the dehydrated hydrogel.

Examples of suitable plasticisers include glycerol, polyethylene glycol, sorbitol and similar sugars, and PLURONIC® brand PEO/PPO polymers.

In a typical method of preparing a dehydrated hydrogel in accordance with the invention, the fibres, polymer and plasticiser in their relative requisite amounts are admixed with water such that the fibres, polymer and plasticiser together provide less than 5% by weight (e.g. less than 3%, e.g. 2%) of the resultant mixture. After thorough mixing, the dispersion may be cast to an appropriate thickness and water evaporated to give a dehydrated hydrogel product containing less than 50% water, more usually 20% or less.

Dehydrated hydrogels in accordance with the invention have a number of advantages. In particular when applied to the wounds (e.g. donor sites, abrasions, dermabrasions, surface wounds with high exudate or wide savings in exudate levels) they are capable of absorbing large amounts of exudate, e.g. up to 30 times their own weight, thereby rehydrating to form a hydrogel. If the dehydrated hydrogel is in the form of a film, it is found that the film swells in the thickness dimension without substantial swelling in the other two dimensions. Upon sufficient absorption of exudate, the film is capable of dissolving. The product of the invention is more absorbent than current commercial hydrogels, and is also light and easy to package.

Dehydrated hydrogels in accordance with the invention may be laminated to hydrophilic films which have an increased breathability in the presence of liquid water as compared to moisture vapour alone. The use of such a film over the dehydrated hydrogel (i.e. on the side remote from the wound) ensures that water is vented from the dehydrated hydrogel through the film. Therefore the dissolution of the hydrogel may be controlled.

Typically the breathable film will be of a material which, as a 50 micron film, has an Moisture Vapor Transfer Rate in the presence of moisture vapour alone of 6,000 to 10,000 g $m^{-2}$ 24 $hr^{-1}$ as measured by ASTM E96B and an MVTR in the presence of liquid water (as measured by ASTM E96BW) of 6,000 to 10,000 g $m^{-2}$ 24 $hr^{-1}$. Typically the breathable film will have a thickness of 30–70 microns, more preferably 40–60 microns, e.g. about 50 microns.

The breathable film may for example be of polyurethane. Suitable films are available from Innovative Technologies Limited under the designations IT325, IT425 and IT625.

If desired, the dehydrated hydrogel may incorporate an active agent (e.g. an antimicrobial material) for delivery to a wound.

DETAILED DESCRIPTION OF PREFERRED EMBODIMENT

The invention will be further described by the following non-limiting Examples.

EXAMPLE 1

7 kg of calcium alginate fibres having a length of 3–6 mm were dispersed in 500 liters of water. Separately, a solution of 3 kg sodium alginate in 60 liters of water was prepared and 10 kg glycerol added thereto. The sodium alginate/glycerol solution and the fibre dispersion were thoroughly mixed and the resultant admixture made up to 1,000 liters.

The mixture was cast at 4 kg/m² to give a thickness of 4 mm. Drying was then effected in an air current under IR at 30° C. so that the film contained less than 50% of water.

The resultant product was a dehydrated hydrogel which was capable of absorbing at least 10 times its own weight of water.

EXAMPLE 2

1 g calcium alginate fibre (chopped into 20 mm lengths) was dispersed into an aqueous medium containing 0.5 g NOCC and 1.5 g glycerol. The resultant mixture was then cast into a 16×23 cm stainless steel dish and the solvent evaporated overnight in an oven at 80° C.

The resultant film had the properties of both NOCC and alginate fibres.

EXAMPLE 3

1 g of calcium alginate fibre (chopped into 20 mm length) was dispersed into 100 ml distilled water. Separately, 0.5 g of sodium alginate powder (Protanal LF10/60 from Pronova Biopolymers) were mixed with 100 ml of distilled water. A third 100 ml portion of distilled water was mixed with 0.15 g acemannan powder (from Carrington Laboratories).

The three liquid were then mixed together with 1.65 g of glycerol. After thorough mixing, the mixture was cast into a 16×23 cm stainless steel disc and the solvent evaporated overnight in an oven at 80° C.

The resultant film comprised a dehydrated hydrogel having the wound healing properties of the acemannan.

What is claimed is:

1. A water absorbable composition containing less than 20% by weight of water that is suitable for use in the treatment of wounds, comprising a dehydrated hydrogel having a cross-linked macro-molecular network, including a precursor polymer, integrated fibres that have donated cations for cross-linking the precursor polymer to form the cross-linked macro-molecular network, and a plasticizer.

2. A composition as claimed in claim 1 in the form of a film.

3. A composition as claimed in claim 2 wherein the film has a thickness of 20 microns to 1 mm.

4. A composition as claimed in claim 1 comprising 15 to 40% by weight of fibres forming the dehydrated hydrogel, 10 to 35% by weight of polymer forming the dehydrated hydrogel and 5 to 75% by weight of plasticiser, the percentages being based on the total weight of fibres and polymer forming the dehydrated hydrogel and of plasticiser.

5. A composition as claimed in claim 4 wherein the fibres and polymer forming the dehydrated hydrogel together provide about 40–60% by weight on the same weight basis as defined in claim 4.

6. A composition as claimed in claim 1 wherein the amount of fibres exceeds the amount of polymer forming the dehydrated hydrogel.

7. A composition as claimed in claim 6 wherein the weight ratio of fibres:polymer forming the dehydrated hydrogel is 1.5–3:1.

8. A composition as claimed in claim 1 wherein the fibres have a length of 1 to 80 mm.

9. A composition as claimed in claim 1 wherein the fibres have a thickness of 10 to 50 microns.

10. A composition as claimed in claim 1 wherein the plasticiser is glycerol, polyethylene glycol, sorbitol or a PEO/PPO polymer.

11. A composition as claimed in claim 1 in which said dehydrated hydrogel in a dehydrated form incorporates acemannan.

12. The composition of claim 11 wherein said dehydrated hydrogel is derived from polymers selected from the group consisting of sodium alginate, sodium carboxymethyl cellulose, sodium pectinate, sodium O-carboxymethyl chitosan (OCC), sodium N,O-carboxymethyl chitosan (NOCC), sodium polyacrylate, and naturally occurring gums and synthetic polymers containing pendant carboxylic acid groups.

13. The compositions of claim 1 wherein said dehydrated hydrogel is derived from sodium alginate and said fibres are calcium alginate fibres.

14. A method of producing a water absorbable composition containing less than 20% by weight of water that is suitable for use in the treatment of wounds, comprising (i) dispersing fibres into an aqueous solution of a hydrogel precursor material incorporating plasticiser, said fibres being capable of donating cations to cross-link said hydrogel precursor material to form a hydrogel;

(ii) effecting formation of a hydrogel by cross-linking of the hydrogel precursor material by cations donated from said fibres so as to form a hydrogel product containing said hydrogel and product fibres derived from the fibres that have donated cations for effecting cross-linking; and (iii) evaporating water from said hydrogel product to produce said composition in the form of a dehydrated hydrogel containing said product fibres.

15. A method as claimed in claim 14 wherein the hydrogel precursor material is selected from the group consisting of sodium alginate, sodium carboxymethyl cellulose, sodium pectinate, sodium O-carboxymethyl chitosan (OCC), sodium N,O-carboxymethyl chitosan (NOCC), sodium polyacrylate, and naturally occurring gums and synthetic polymers containing pendant carboxylic acid groups.

16. A method as claimed in claim 14 wherein the fibres contain $Ca^{2+}$, $Zn^{2+}$ or cations which also act as enzyme cofactors.

17. A method as claimed in claim 16 wherein the fibres are calcium alginate fibres.

18. A method as claimed in claim 17 wherein the hydrogel precursor material is sodium alginate.

19. A method of producing a water absorbable composition containing less than 20% by weight of water that is suitable for use in the treatment of wounds, comprising (i) dispersing calcium alginate fibres into an aqueous solution of sodium alginate incorporating plasticiser, said calcium alginate fibres being capable of donating calcium ions to cross-link said sodium alginate to form a hydrogel;

(ii) effecting formation of a hydrogel by cross-linking of the sodium alginate by calcium ions donated from said fibres so as to form a hydrogel product containing said hydrogel and product fibres derived from said calcium alginate fibres cations that have donated cations for effecting cross-linking; and (iii) evaporating water from said hydrogel product to produce said composition in the form of a dehydrated hydrogel containing said product fibres.

20. A method of producing a water absorbable composition containing less than 20% by weight of water that is suitable for use in the treatment of wounds, comprising
   (i) dispersing fibres into an aqueous solution of a hydrogel precursor material incorporating plasticiser, said fibres being capable of donating cations to cross-link said hydrogel precursor material to form a hydrogel;
   (ii) casting the composition resulting from step (i) into a form for producing a film in step (iii)
   (iii) effecting formation of a hydrogel by cross-linking of the hydrogel precursor material by cations donated from said fibres so as to form a film of a hydrogel product containing said hydrogel and product fibres derived from the fibres that donated cations for effecting cross-linking; and
   (iv) evaporating water from said hydrogel product to produce a film of said composition in the form of a dehydrated hydrogel containing said product fibres, said film being capable on absorption of wound exudate of swelling in the thickness dimension without substantial swelling in the other two dimensions.

21. A method as claimed in claim 20 wherein the hydrogel precursor material is sodium alginate and the fibres are calcium alginate fibres.

22. A water absorbable composition suitable for use in the treatment of wounds, said composition containing less than 20% moisture and being in the form of a film, the composition comprising a dehydrated hydrogel having a cross-linked macromolecular network, including a precursor polymer, integrated product fibres derived from fibres that have donated cations for cross-linking the precursor polymer to form the cross-linked macromolecular network, and a plasticiser, said film being capable of an absorption of wound exudate of swelling in the thickness dimension without substantial swelling in the other two dimensions.

23. A composition as claimed in claim 22 wherein the precursor polymer is sodium alginate and the product fibres are derived from calcium alginate fibres.

* * * * *